(12) United States Patent
Kim et al.

(10) Patent No.: US 9,861,939 B2
(45) Date of Patent: Jan. 9, 2018

(54) FILTRATION DEVICE FOR RAPID SEPARATION OF BIOLOGICAL PARTICLES FROM COMPLEX MATRICES

(71) Applicant: LAWRENCE LIVERMORE NATIONAL SECURITY, LLC, Livermore, CA (US)

(72) Inventors: Sangil Kim, Pleasanton, CA (US); Pejman Naraghi-Arani, Dublin, CA (US); Megan Liou, San Ramon, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 213 days.

(21) Appl. No.: 14/874,326

(22) Filed: Oct. 2, 2015

(65) Prior Publication Data

US 2017/0095772 A1    Apr. 6, 2017

(51) Int. Cl.
| | |
|---|---|
| *B01D 35/00* | (2006.01) |
| *B01D 65/02* | (2006.01) |
| *B01D 61/00* | (2006.01) |
| *B01D 61/42* | (2006.01) |
| *C12N 13/00* | (2006.01) |

(52) U.S. Cl.
CPC .......... *B01D 65/02* (2013.01); *B01D 61/002* (2013.01); *B01D 61/427* (2013.01); *C12N 13/00* (2013.01); *B01D 2317/02* (2013.01)

(58) Field of Classification Search
None
See application file for complete search history.

(56) References Cited

U.S. PATENT DOCUMENTS

| | | | |
|---|---|---|---|
| 2006/0054557 A1 | 3/2006 | Hori et al. | |
| 2011/0100920 A1 | 5/2011 | Messier | |
| 2014/0231351 A1 | 8/2014 | Wickramasinghe et al. | |
| 2014/0271767 A1* | 9/2014 | Askari ............... A61L 26/0066 424/422 |

FOREIGN PATENT DOCUMENTS

| | | |
|---|---|---|
| WO | 2012019103 A2 | 2/2012 |
| WO | 2013101857 A1 | 7/2013 |

OTHER PUBLICATIONS

International Search Report and Written Opinion for International Application No. PCT/US2016/054331 filed Sep. 29, 2016 on behalf of Lawrence Livermore National Security, LLC. dated Jan. 16, 2017. 11 pages.

Moon et al. "Capture and alignment of phi29 viral particles in sub-40 nanometer porous alumina membranes" Biomed Microdevices. Feb. 2009; 11(1): 135-142.

(Continued)

*Primary Examiner* — Jill Warden
*Assistant Examiner* — Brittany Fisher
(74) *Attorney, Agent, or Firm* — Steinfl + Bruno, LLP

(57) ABSTRACT

Methods and systems for filtering of biological particles are disclosed. Filtering membranes separate adjacent chambers. Through osmotic or electrokinetic processes, flow of particles is carried out through the filtering membranes. Cells, viruses and cell waste can be filtered depending on the size of the pores of the membrane. A polymer brush can be applied to a surface of the membrane to enhance filtering and prevent fouling.

15 Claims, 10 Drawing Sheets

(56) References Cited

OTHER PUBLICATIONS

Park et al. "Continuous dielectrophoretic bacterial separation and concentration from physiological media of high conductivity" Lab Chip. Sep. 7, 2011;11(17):2893-900.
Hwang et al. "Rapid detection of bacterial cell from whole blood: Integration of DNA sample preparation into single micro-PCR chip" Sensors and Actuators B Chemical, Jan. 2009, 154(1):46-51.
Zhang et al. "Development of a virus concentration method using lanthanum-based chemical flocculation coupled with modified membrane filtration procedures" J. Virol. Methods, Jun. 2013, 190(1-2): 41-48 Abstract Only.

* cited by examiner

FILTRATION DEVICE FOR RAPID SEPARATION OF BIOLOGICAL PARTICLES FROM COMPLEX MATRICES

STATEMENT OF INTEREST

The United States Government has rights in this invention pursuant to Contract No. Contract No. DE-AC52-07NA27344 between the U.S. Department of Energy and Lawrence Livermore National Security, LLC.

TECHNICAL FIELD

The present disclosure relates to filtration of biological particles. More particularly, it relates to a filtration device for rapid separation of biological particles from complex matrices.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
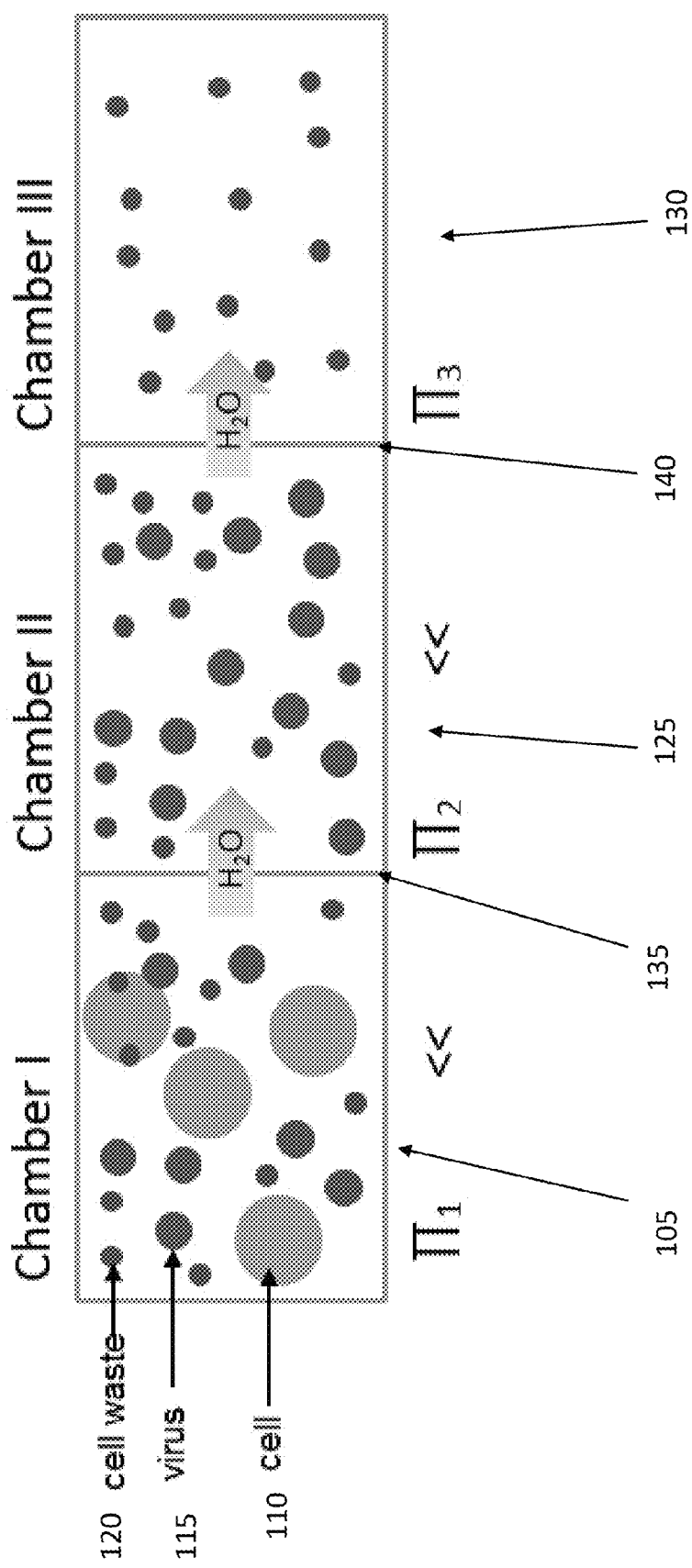
FIG. 1 illustrates an overview of one embodiment of the filtering process of the present disclosure.

In a first aspect of the disclosure, a device is described, the device comprising: a plurality of chambers; at least one filtering membrane between a first chamber and a second chamber of the plurality of chambers, the at least one filtering membrane having a pore size based on a desired biological particle to be filtered; and at least one polymer brush layer, attached to the at least one filtering membrane on a side downstream to a fluidic flow between the first chamber and the second chamber.

In a second aspect of the disclosure, a method is described, the method comprising providing a plurality of chambers, at least one filtering membrane between a first chamber and a second chamber of the plurality of chambers, the at least one filtering membrane having a pore size based on a desired biological particle to be filtered, at least one polymer brush layer, attached to the at least one filtering membrane on a side downstream to a fluidic flow between the first chamber and the second chamber; inserting a solution containing biological particles in the first chamber of the plurality of chambers; driving the fluidic flow through the plurality of chambers; and extracting the desired biological particle after filtering through the plurality of chambers.

BACKGROUND

Different filtration processes can be used to filter biological particles in a fluid. For example, the use of nanoporous aluminum oxide membranes is described in Ref. [1]. The membranes have a pore size between 70 and 15 nm and are fabricated by atomic layer deposition. The membranes are used together with centrifugation methods. Dielectrophoresis is used in Ref [2] within a microfluidic device, with a filtering efficiency of 97%. The device comprises two channels with several dielectrophoresis elements that separate and concentrate target particles. Ref [3] describes the use of surface-modified micropillars possessing affinity for bacterial cells, fabricated inside a PCR chip. Pillars with a square cross section are used for particle capture. Ref. [4] describes a lanthanum-based flocculation method coupled with a $Mg^{2+}$-modified membrane filtration procedure. The flocculation step is applied to reduce the solution volume, followed by a two-step membrane filtration. One of the membrane steps comprises centrifugation.

DETAILED DESCRIPTION

The present disclosure describes the development of a rapid purification/concentration device for biological particles (e.g. DNA, viruses, bacteria), comprising a functionalized membrane filter using osmosis or an electric potential as a driving force. The polyethylene glycol (PEG)-functionalized nanoporous membrane provides high viral separation efficiency without clogging the membrane pores. This can be achieved because of the strong hydration of the functional polymers layer that is added to the filtering membranes, and its resistance to protein adsorption. In addition, an osmosis process or an electrokinetic process can be employed for moving the solution through the filtering membranes, which does not require any external complex equipment (e.g. vacuum pump, centrifuge).

The devices of the present disclosure can be used to develop a simple diagnostic platform for rapid detection of bloodstream infections. Other uses may comprise polymerase chain reaction sample preparation, point-of-care diagnosis, viral separation and concentration, bacterial separation and concentration, and membrane filtration.

The devices of the present disclosure can be used for the development of novel viral sample preparation techniques from blood samples, for improved detection and identification of rare biological particles. Conventional laboratory diagnostics based on culture or molecular methods need prolonged assay time and complex processing by skilled technicians using costly large-scale instrumentations in centralized laboratories. This can lead to physicians making treatment decisions based on an incomplete diagnosis contributing to patient morbidity. Ideally a diagnostic platform should be simple, rapid, reliable, and be able to be processed by non-technical staff even in a non-hospital setting where immediate clinical decision-making can be life-saving. Thus, rapid and reliable detection of bloodstream infections can gain from the improved and straightforward isolation of highly purified viruses from whole blood.

The direct membrane filtration method is often used to concentrate pathogens (viruses or bacteria) because it is fast, safe, and easy to use. However it may suffer from severe membrane fouling and clogging. Hence, the ideal membrane for this application needs to incorporate an anti-fouling functionality to effectively separate biological particles from blood cells or cell waste. Without anti-fouling coatings, pathogens or blood cells rapidly clog the membrane pores or surfaces and stop the separation process, thus resulting in a reduced viral separation process speed and low viral purity.

By incorporating a poly (ethylene glycol) methacrylate (PEGMA) functionalized membrane into a microfluidic device it is possible to fabricate a viral filtration device with high viral retention and recovery. The PEG-functionalized nanoporous membrane provides high biological particles separation efficiency because of strong hydration of the functional polymer layer and its resistance to protein adsorption. The present disclosure describes innovative pathogens purification/concentration routes based on functionalized membranes and forward osmosis (FO) processes. Unlike other pressure-driven membrane filtration processes, the FO process is an osmotically driven natural separation process requiring no energy for separation.

In some embodiments, the devices of the present disclosure comprise three chambers: 1) a feed and blood cells chamber (105), 2) a viral concentration chamber (125), and 3) a cell waste chamber (130). Each chamber is divided from the others by membranes (135, 140) with different pore sizes. The chambers can be filled with an electrolyte or draw solution to transport target solutes. The embodiments described below with reference to FIGS. 1-4 should be considered an example. In other embodiments, a different number of chambers may be used, for example two, or four. The progressive filtration from the first chamber to the last chamber can be carried out by progressively reducing the size of the pore of the filtering membranes, in order to progressively filtering out smaller particles. In this way, different particles can be filtered. For example, in one embodiment the target particle can be a virus, while in other embodiments the target particle may be a cell or other biological particle. Therefore, the size of the pores can be adjusted based on what particles needs to be filtered.

In the embodiment of FIG. 1, the first chamber (105) can contain cell waste (120), viruses (115), and cells (110). The second chamber (125) can contain viruses and cell waste, as the cells in the first chamber have been filtered by the membrane (135). The third chamber (130) can contain cell waste, as the viruses in the second chamber have been filtered by the membrane (140). The first membrane (135) can have a different pore size compared to the second membrane (140). In other embodiments, a different number of chambers or membranes may be used, according to the type of biological particles within the chambers, and the type of filtering that is specified for that application.

In general, overall rate of solute transport through porous membrane is given by the sum of the diffusive and convective contributions, and the convective transport of solute is much higher than the diffusive transport. In the present disclosure, the osmotic pressure difference induced by the draw solution is a primary driving force for separating viral particles and cell wastes from blood cells, and offers a simple filtration device requiring no pumps or energy. Pathogens (virus or bacteria) and small size proteins, such as cell waste, can be separated from blood cells; these biological particles move fast in high water flux streams to the second chamber by convective transport caused by osmotic pressure differences. For example, a track-etched membrane with a 1 micrometer pore size can transport $6.0 \times 10^8$ virus/cm$^2$ sec even at a pressure difference $\Delta P=1$ bar. Cell waste can also be separated from pathogen particles in a second chamber, due to the fact that an increased amount of water, relative to the number of particles, lowers the osmotic pressure in the second chamber. The decrease in osmotic pressure will cause an osmotic pressure difference between the second and third chambers. To keep pathogens in the second chamber and allow only small protein transport to the third chamber, a membrane with a smaller pore size can be used (e.g. <30 nm). Therefore, in some embodiments, the first membrane will have a higher pore size relative to the second membrane. An attached polymer brush (e.g. PEGMA, PEG) can prevent back-diffusion of separated solutes and fouling of proteins on the membrane surface, which would clog membrane pores. In some embodiments, the polymer brush can be attached to a surface of the membrane, for example on the surface downstream to the increasingly filtrated succession of chambers. For draw solutions development, magnetic nanoparticles (MNP), polymer hydrogel, or a combination can be used.

Figure 2:
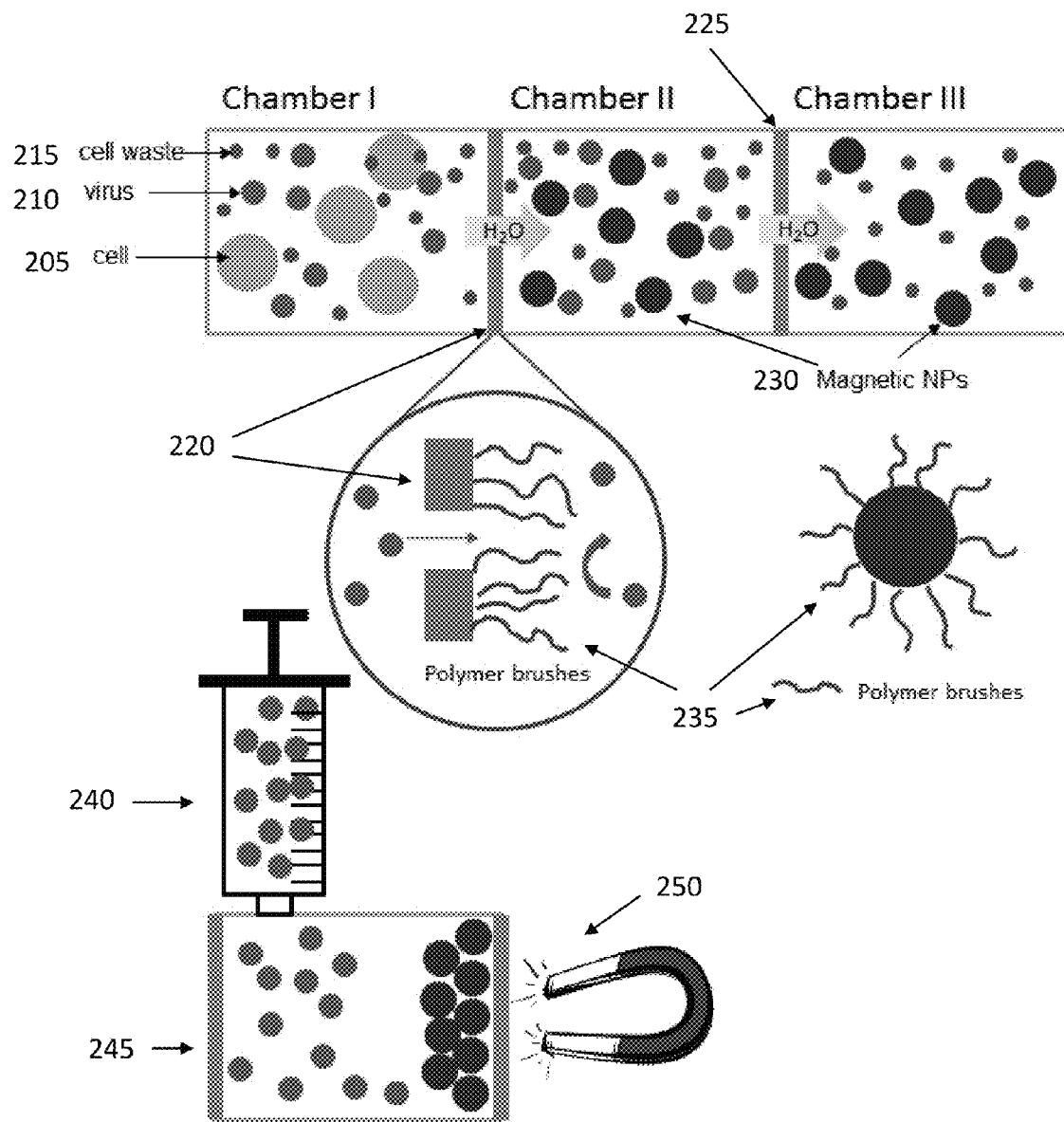
FIG. 2 illustrates an example of filtering based on nanoparticles.

For example, in FIG. 2 an exemplary arrangement is illustrated, with a first chamber containing cells (205), viruses (210) and cell waste (215). The second chamber can contain viruses and cell waste, together with magnetic nanoparticles (230). A filtering membrane (220) is situated between the first and second chambers. A polymer brush (235) can be attached to the surface of the membrane (220) that faces the second chamber. The polymer brush (235) can prevent the viruses and cell waste from moving back into the first chamber. The polymer brush (235) can also prevent fouling of the filtering membrane. Osmotic pressure, in some embodiments, can be used for moving particles through the filtering membrane. Another filtering membrane (225) can separate the second and third chamber. This second membrane can also, in some embodiments, have a polymer layer on a surface.

In some embodiments, highly water-soluble magnetic nanoparticles can be used to aid in the filtering process. The MNPs can be functionalized with various groups (e.g. PEG, PEGMA, polyacrylic acid) and can be used as a draw solution to yield a driving force and high water flux through the filtering membranes. MNPs with different diameters and functional groups can be used to control osmosis in the chamber. The functional groups attached on the MNPs can prevent adsorption of biomolecules on the MNPs. The separated target solutes in each chamber and the MNPs can be separated by a magnetic field, and the captured MNPs can be recycled after regeneration procedures (e.g. chemical treatment or high temperature treatment).

For example, with reference to FIG. 2, polymer brushes can be attached to magnetic particles (230). The magnetic nanoparticles can be separated from the other particles inside a chamber (245) through the application of a magnetic field (250). The magnetic field will attract the magnetic nanoparticles to a side of the chamber, for example. A sample can be inserted in the chamber (245), for example through a plunger (240).

In some embodiments the polymer functional groups (e.g. PEG, PEGMA) can be attached to the surface of the magnetic nanoparticles. This arrangement can 1) yield a driving force as a draw solution by increasing molar concentration and osmotic pressure in the solution; 2) enhance dispersion of the MNPs 3) prevent adsorption of biomolecules onto the MNPs.

As known to the person skilled in the art, an increase in particle concentration causes an increase in osmotic pressure, which entails a movement of water from the region with lower osmotic pressure to the region with a higher osmotic pressure. When magnetic nanoparticles are well dispersed in a solution, they increase the molar concentration of the solution, in turn leading to an increase in osmotic pressure of the solution according to the Morse equation: Phi=CRT, where Phi is the osmotic pressure, C is the molar concentration, R is the gas constant, and T is the absolute temperature. The osmotic pressure difference between two phases (separated by a semipermeable membrane) is a driving force for water transport. Water in the low osmotic pressure side transports to the solution with the high osmotic pressure side to reach equilibrium. The side with higher osmotic pressure can be termed the draw solution. Dispersion of MNPs can be enhanced by surface modification with hydrophilic polymer brushes (such as PEG or PEGMA). This effect can be similar to adding surfactant to disperse hydrophobic nanoparticles in water. Therefore, the polymer brushes can enhance dispersion and increase osmotic pressure.

Since the magnetic nanoparticles can be separated from the solution with a magnetic field, the MNPs can be advantageously applied to regulate the osmotic pressure, and later removed from the solution.

In some embodiments, polymer hydrogels can be used as draw agents for forward osmosis. Polymer hydrogel particles or scaffolds can be used as a draw agent in the FO process of viral purification/separation. Polymer hydrogels, which are formed of loosely hydrophilic cross-linked polymers, have the capacity to undergo drastic changes in volume by absorbing and retaining large amounts of water, while still remaining insoluble. This mechanism can provide a sufficient driving force to develop a high water flux. Different chemical compositions of hydrogels can be synthesized by free-radical polymerization of different monomers and the crosslinker, to achieve the flexibility and hydrophilicity of the polymer network that will control osmotic pressure in the chamber. At the same time, the hydrogels should not bind to the biological particles as that would result in fouling of the hydrogel as well as loss of the filtered particles.

Figure 3:
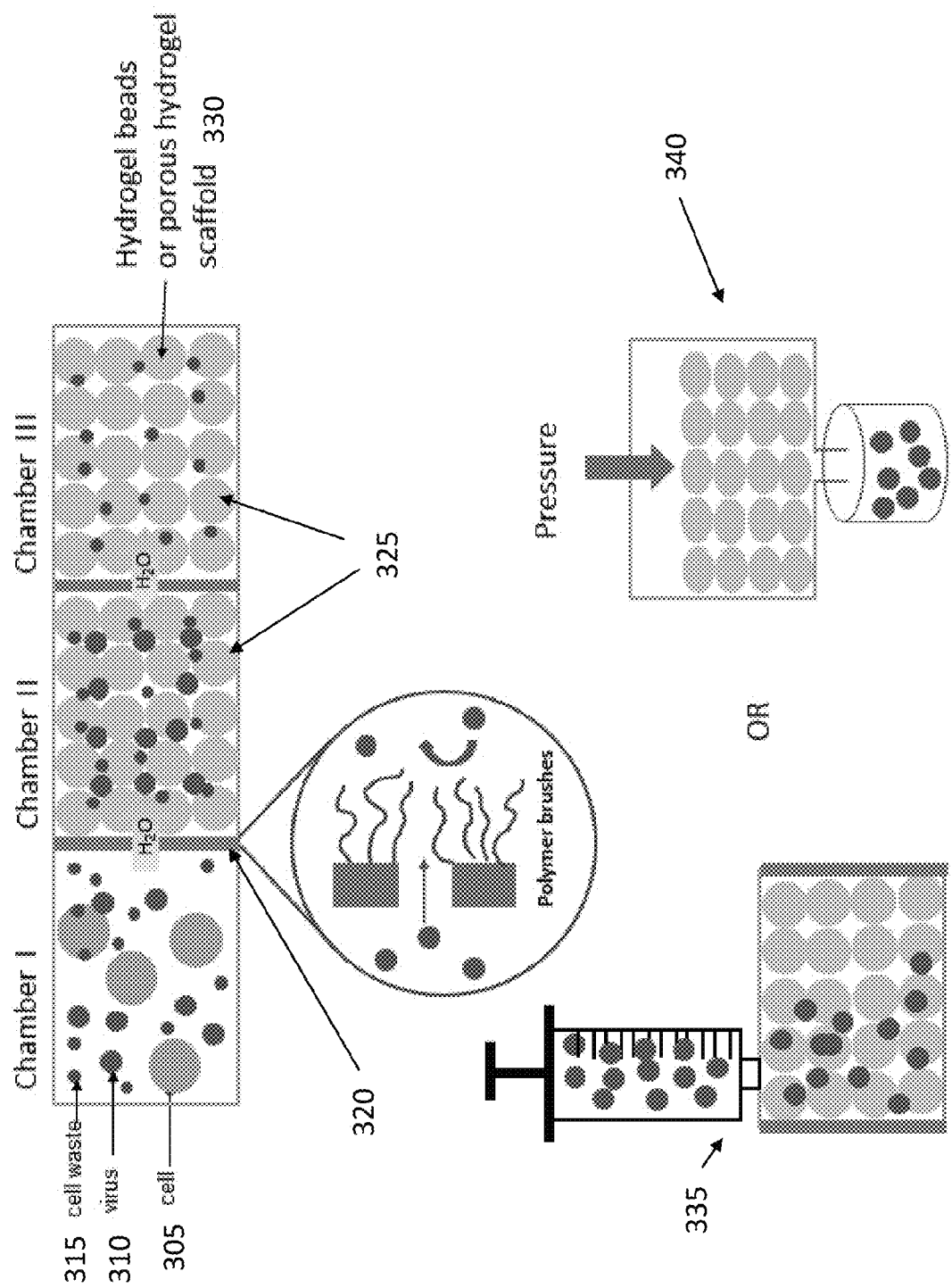
FIG. 3 illustrates an example of filtering based on hydrogels.

For easy extraction of separated solutes from swollen hydrogels, a hydrogel scaffold can be used. Solutes entrapped in a large macroporous scaffold can be easily collected and concentrated with syringes, for example. As the person of ordinary skill in the art will understand, a polymer scaffold is a scaffold structure, for example formed by small fibers in a three dimensional structure. In some embodiments, hydrogel beads (325) can be used. Hydrogel beads or a porous hydrogel scaffold (330) can be used. A filtering membrane (320) can comprise a polymer brush on one surface, similarly to the embodiment of FIG. 2. In FIG. 3, cells (305), viruses (310) and cell waste (315) can be filtered.

As visible in FIG. 3, particles can be inserted in, or removed from, a chamber through a plunger (335) or other pressure-drive processes (340). In other embodiments, the filtering devices of the present disclosure can be based on an electrokinetic process.

Figure 4:
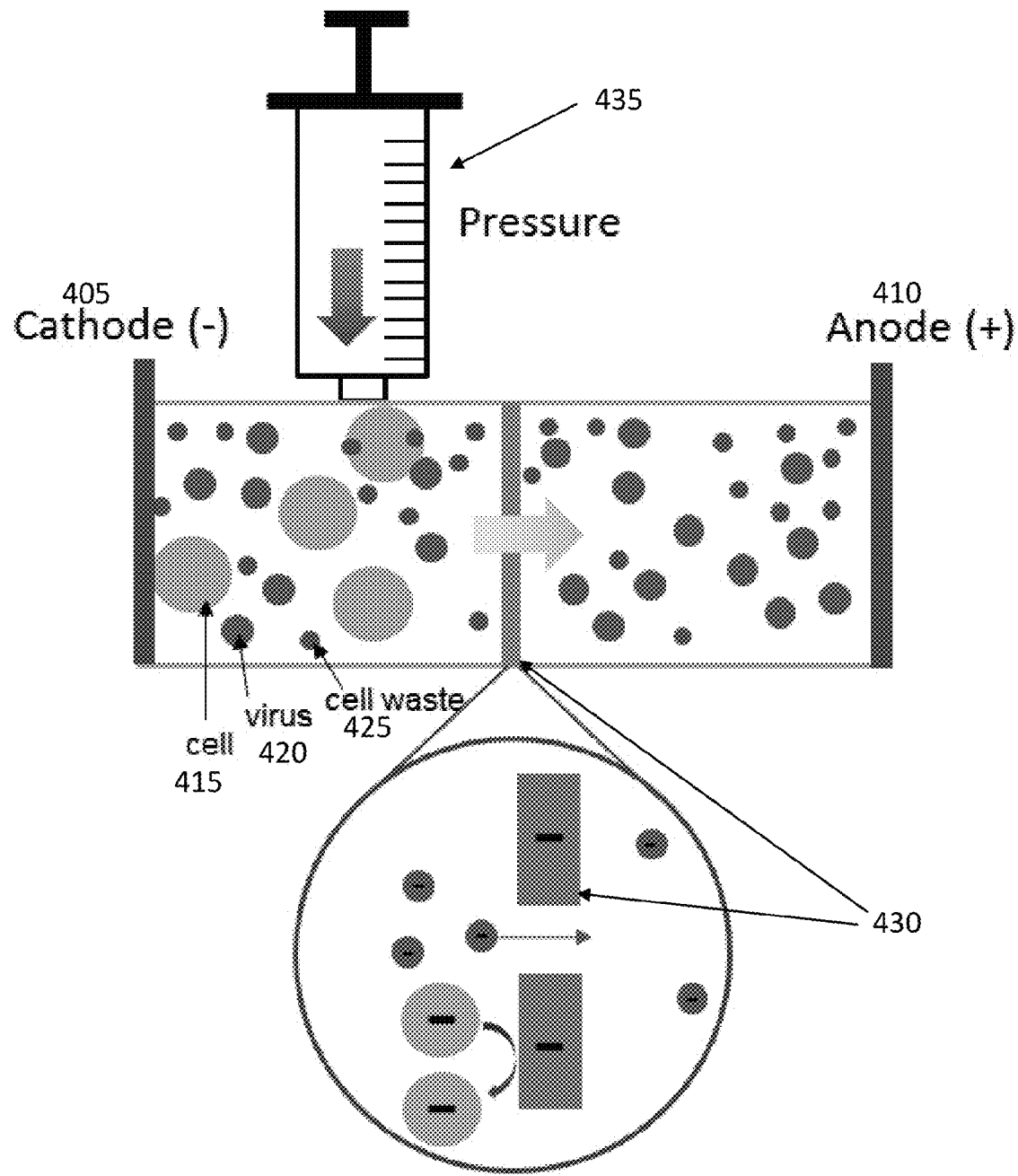
FIG. 4 illustrates an example of filtering based on an electrokinetic process.

Microscale electrokinetic techniques have great potential for the separation and sorting of microorganisms, and can meet the need for rapid and early detection of pathogens in medical diagnostics applications. The application of a direct current between two electrodes, for example as seen in FIG. 4 (405, 410), creates three main effects: electroosmosis (the movement of water towards the cathode 405), electromigration (the movement of ionic species to the electrode that is oppositely charged with respect to the ionic species), and electrophoresis (the transport of charged particles or colloids to the electrode that is oppositely charged with respect to the charged particles). The use of an electric field to enhance bacterial movement can be employed, for example, for the application of soil remediation. Therefore, the presence of an electric field in the solution has three effects: electroosmosis, electromigration and electrophoresis.

In this embodiment, an electric potential (for example, a voltage of 9 V) can be used as a main driving force to separate target pathogens (viruses or bacteria) in the device with an incorporated functionalized membrane. Depending on the surface charge of the membrane pore walls, electroosmosis may enhance or counteract electrophoresis. However, electroosmotic water flow should not be expected to occur to a great extent in the device due to the relatively high permeability of track-etched membranes with micrometer-sized pores. Most membranes of this type have a surface with a net negative charge, at high pH, and a net positive charge at low pH. The higher the pH, the greater the negative surface charges, which will increase electrophoretic mobility of biomolecules. In addition to increasing electrophoretic mobility, an increase in the negative surface charge on the viruses or bacteria cells can increase the electrostatic repulsion between the viruses or bacteria cells and the surface of the membrane, therefore decreasing adsorption and fouling of viruses or bacteria on the membrane surface. Therefore, a suitable voltage and/or pH can be employed, in some embodiments, to control fouling or clogging of a filtering membrane.

In order to achieve a maximum separation rate of pathogen particles (virus or bacteria), a low pressure can be used in the filtering process, for example as applied from a plunger (435). Although the applied pressure is low, the use of pressure combined with electrokinetic forces acting on viral (or bacteria) particles will significantly enhance transport of viral (or bacteria) particles. Parameters ruling electroosmotic and electrophoretic velocity (such as pH, electrolyte concentration, electric potential, and pore size/charge properties of membrane) can be controlled to ensure effective separation of pathogens from blood cells.

In FIG. 4, cells (415), viruses (420) and cell waste (425) can be filtered through a membrane (430). The membrane (430) can be electrically charged.

Figure 5:
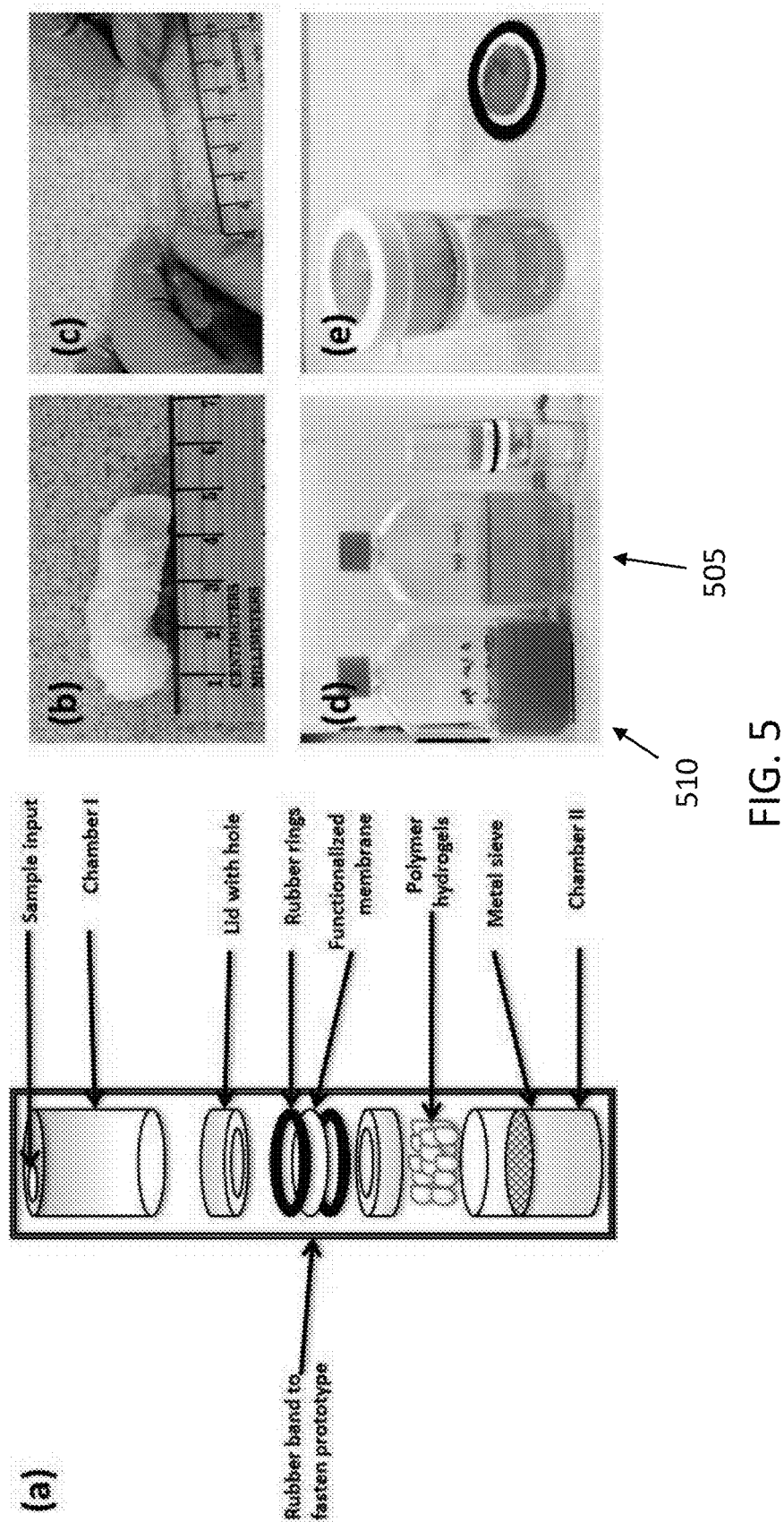
FIG. 5 illustrates an exemplary chamber.

FIG. 5 illustrates an exemplary chamber and contains several panels: (a) Illustration of the device, (b) freeze dried hydrogel, (c) wet hydrogel demonstrating good elastic properties, (d) experimental setup for dye test, 6 um (505) and 0.2 um (510), and (e) filtration performance of the device. The device with a functionalized membrane with 5 um pore size completely excluded red dye particles with a filtration rate greater than 1 ml/min.

Through experimental testing, optimized polymer hydrogels were created that had optimized balance between absorption and mechanical properties that conducted forward osmosis but eluted sample without external pressure. For practical applications, assembly of this embodiment could require two chambers, where small target components (e.g. virus, bacteria) are separated from large components (e.g. cells) and passed through the functionalized membrane. The separation process takes advantage of both hydrogel-based mass transports and gravitation. Target components were collected through the device embodiment of FIG. 6.

Figure 6:
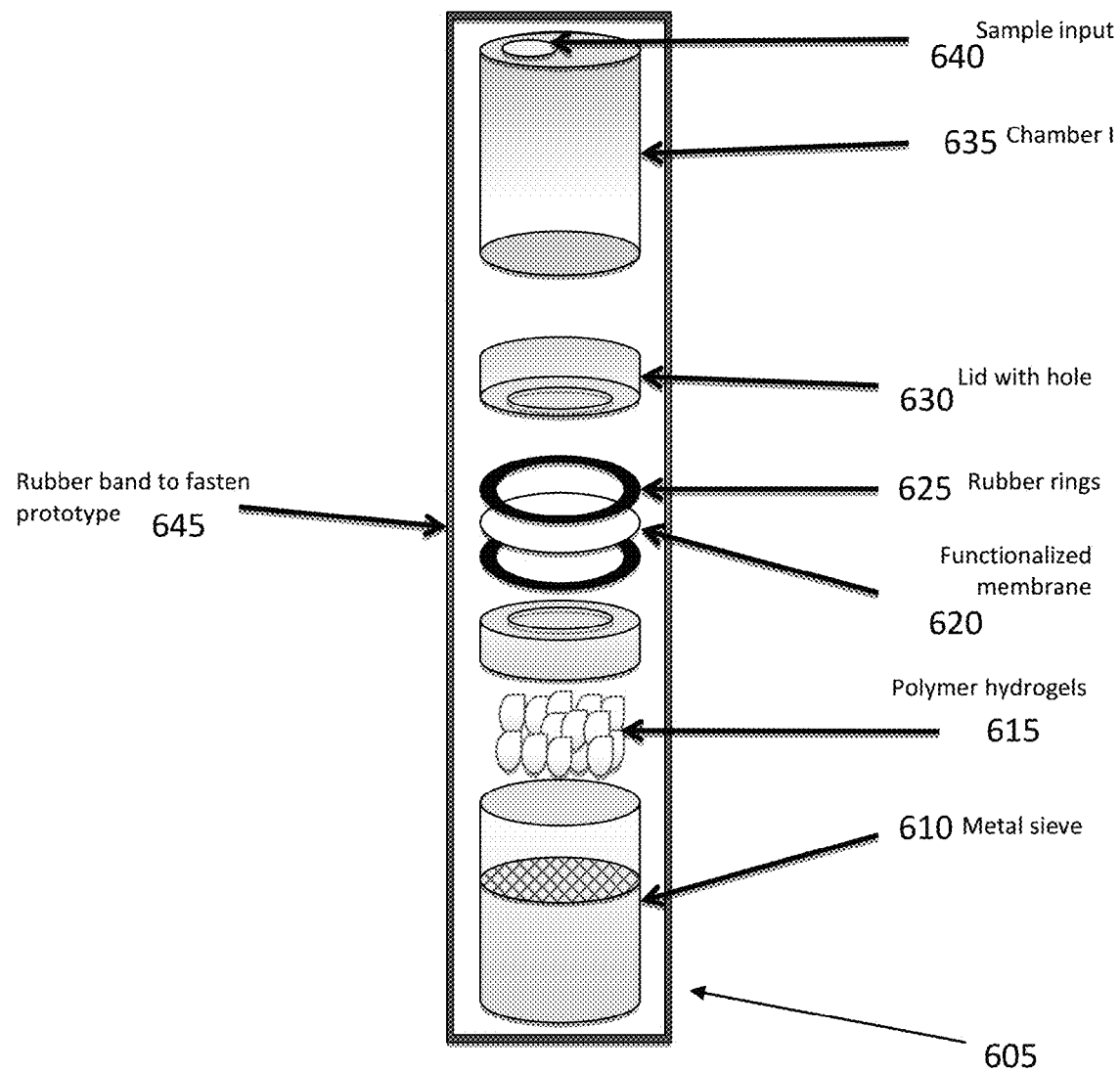
FIG. 6 illustrates a device embodiment.
Figure 7:
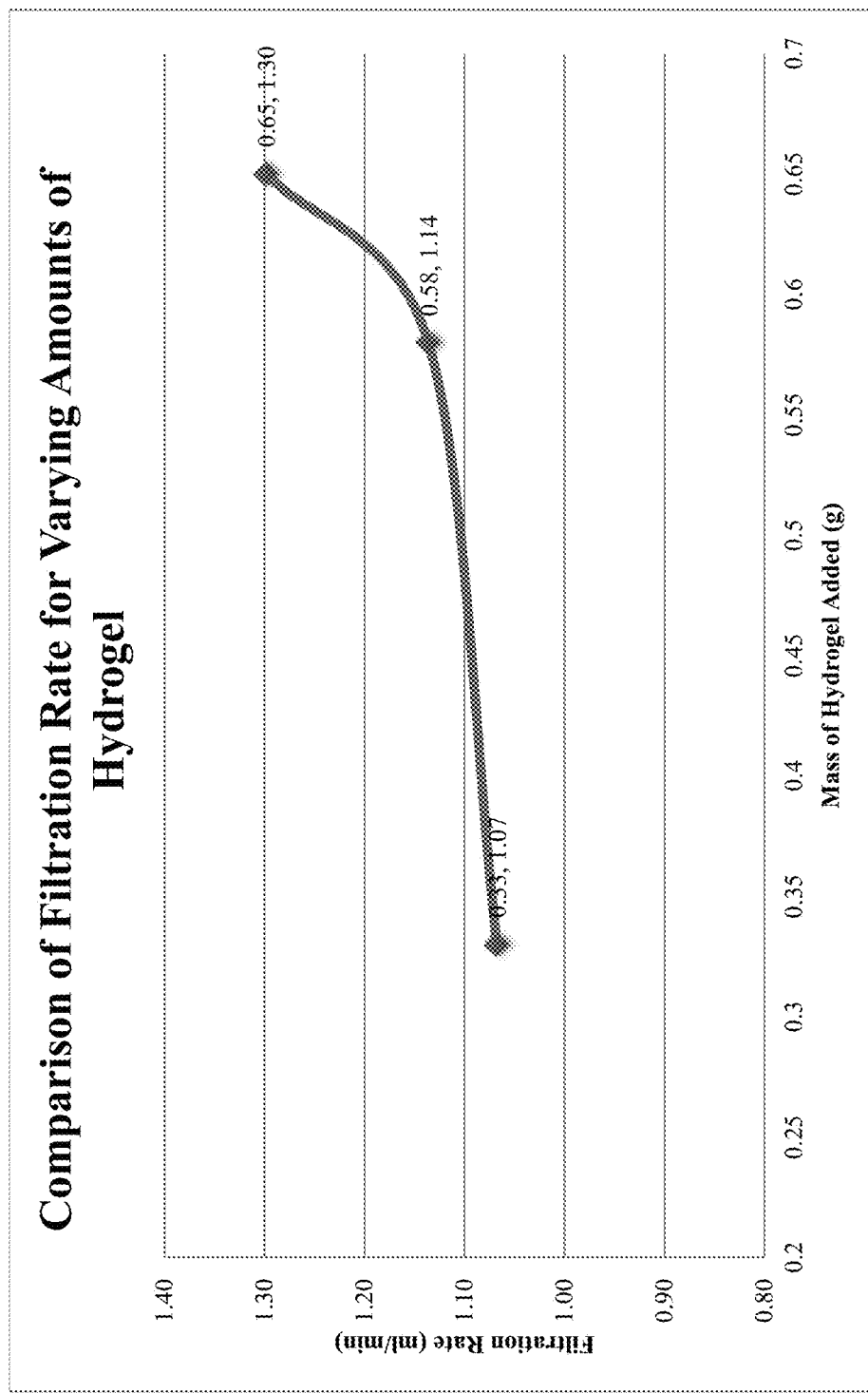
FIGS. 7-10 illustrate experimental results.
Figure 8:
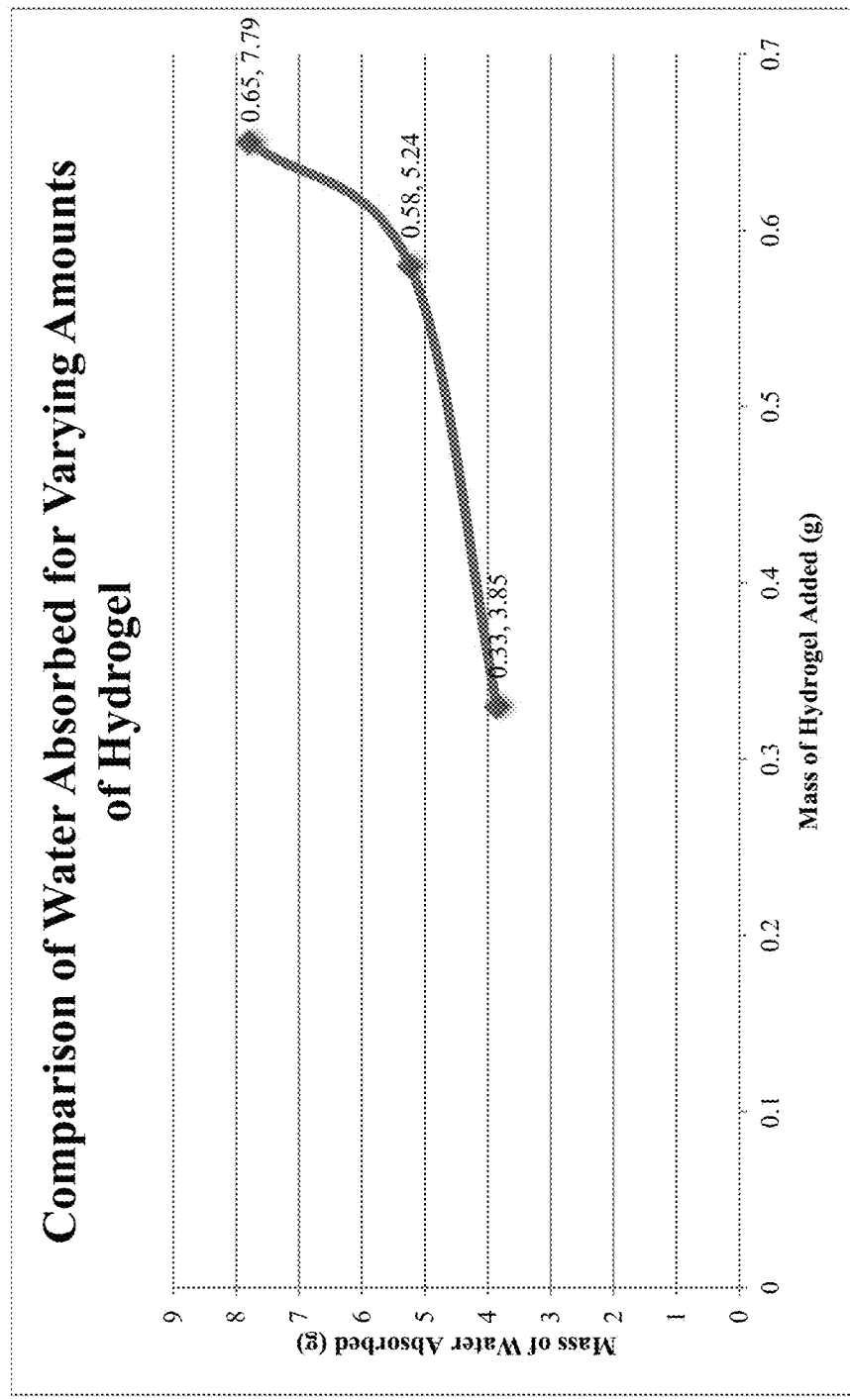
Figure 9:
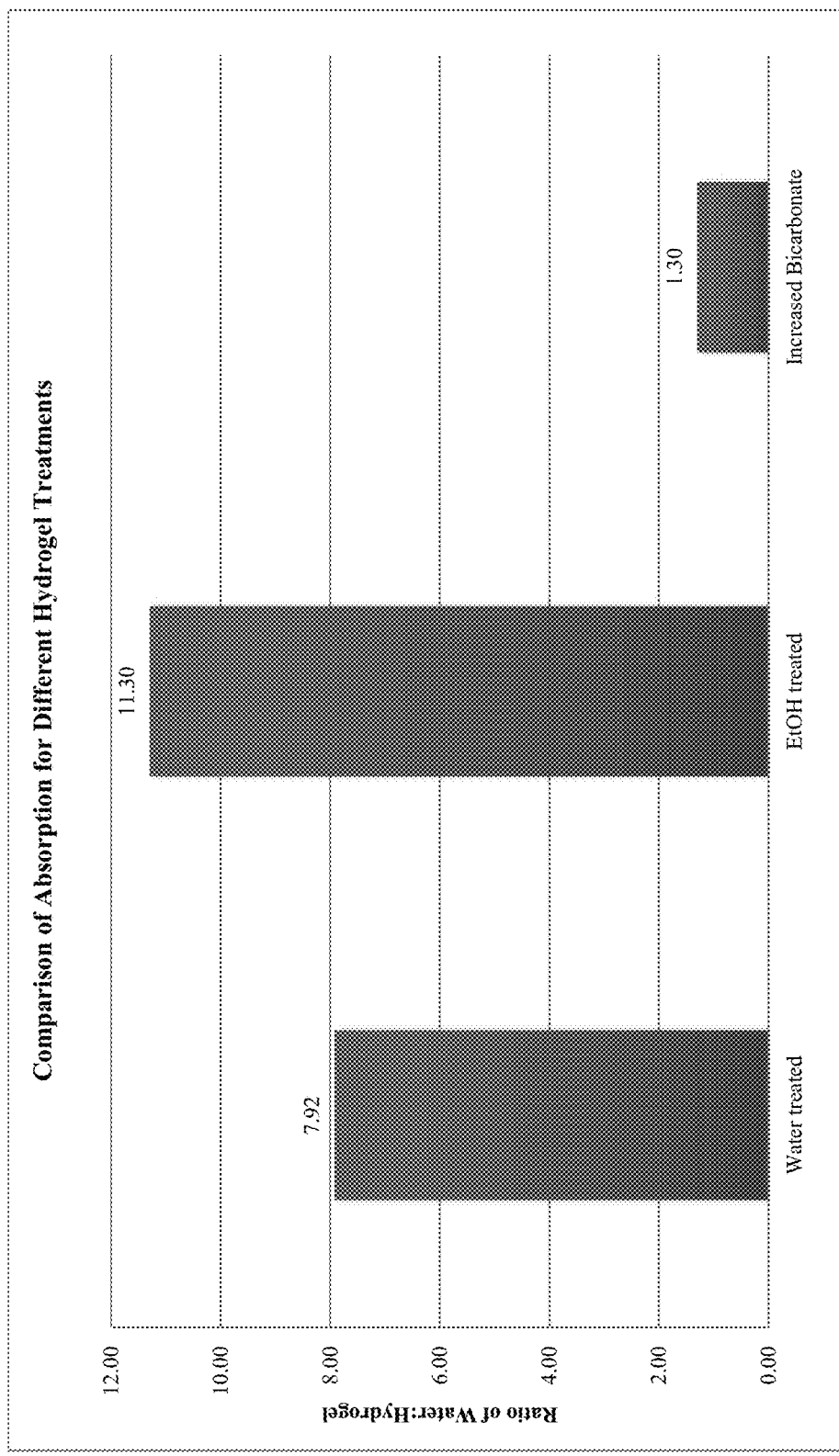
Figure 10:
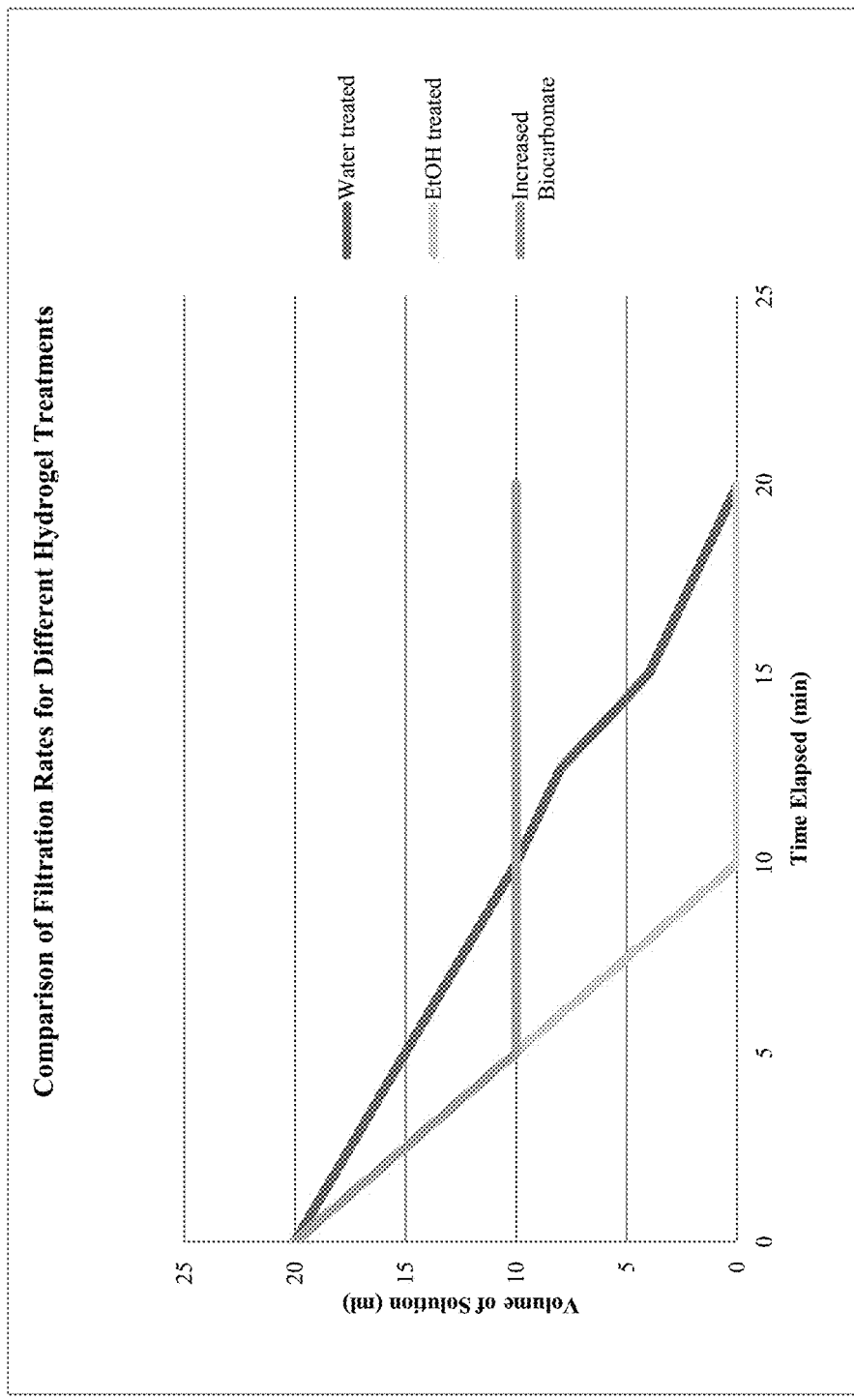

In FIG. 6 a sample can be introduced in a top chamber (chamber I, 635) through an opening (640). A lid with a hole (630) can be sealed with a rubber ring (625), and the sample can be flown through a functionalized membrane (620), a polymer hydrogel (615) and a metal sieve (610). A bottom chamber (chamber II, 605) can collect the specimen of interest. A rubber band (645) is used in an embodiment to hold the chambers together.

The sample can be loaded through an input hole in chamber I (635), where it would pass through a functionalized membrane that separates large particles from small particles in solution. The membrane contains polymer brushes on its surface to prevent clogging pores with larger particles in the sample. High water flux is maintained through driving forces from the packed polymer hydrogels and through gravitational pull. As filtrate is passed through the membrane, it drips from saturated hydrogels and collects in chamber II (605).

Experiments filtering a 10 ml mixture of water, 6 um red nanoparticles, and 0.2 um blue nanoparticles through either a functionalized membrane or non-functionalized membrane demonstrated the importance of using functionalized membranes. Filtrate collected from filtration using non-functionalized membrane was clear and displayed a lack of nanoparticles in solution. This was further bolstered through the aggregation of red and blue nanoparticles on the used non-functionalized membrane, indicating extensive clogging by using non-functionalized membranes. However, filtrate collected from filtration using functionalized membranes was blue, indicating a successful separation of large red particles from small blue particles. In addition, the aggregation of red nanoparticles on the functionalized membrane demonstrated successful filtration and lack of clogging as the mixture passed through the membrane.

Experiments filtering a 10 mls mixture of water, 6 um red nanoparticles, and 0.2 um blue nanoparticles through a functionalized membrane with varying amounts of packed polymer hydrogels demonstrated amounts of hydrogel needed for the target water flux of 1 ml/min. Filtration rate, calculated by total volume filtered over total time elapsed, for each amount of hydrogel added showed water flux increased as more hydrogel was added. In addition, only 0.33 g hydrogel was necessary to reach target water flux. Experimental results are visible in FIGS. 7-10.

In the same aforementioned experiment, water absorbed for each amount of hydrogel added showed water absorption increased as more hydrogel was added. This indicates hydrogels are consistently capable of absorbing 10$x$ their mass of water. This finding not only further corroborated the positive relationship between filtration rate and mass of hydrogel added but also suggested potential for the filtration prototype to concentrate sample filtrate.

Another experiment compared absorption for hydrogels with different composition. 20 mls mixtures of water, 6 um red nanoparticles, and 0.2 um blue nanoparticles were filtered through a functionalized membrane with packed polymer hydrogels of varying composition. Water treated hydrogels served as the control, ethanol treated hydrogels dissolved unreacted monomers and increased mechanical strength of the hydrogels, and increased bicarbonate concentration expanded hydrogel pore sizes to create denser hydrogels. Experimental data indicated ethanol treated hydrogels were the most absorbent.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

[1] Moon et al., Capture and alignment of phi29 viral particles in sub-40 nanometer porous alumina membranes, Sep. 4, 2008, Biomed Microdevices (2009) 11:135-142
[2] Park et al., Continuous dielectrophoretic bacterial separation and concentration from physiological media of high conductivity, Apr. 11, 2011, Lab Chip, 2011, 11, 2893
[3] Hwang et al., Rapid detection of bacterial cell from whole blood: Integration of DNA sample preparation into single micro-PCR chip, May 20, 2011, Sensors and Actuators B 154 (2011) 46-51
[4] Zhang et al., Development of a virus concentration method using lanthanum-based chemical flocculation coupled with modified membrane filtration procedures, Apr. 1, 2013, Journal of Virological Methods 190 (2013) 41-48

What is claimed is:
1. A device comprising:
a plurality of chambers;
at least one filtering membrane between a first chamber and a second chamber of the plurality of chambers, the at least one filtering membrane having a pore size based on a desired biological particle to be filtered;
at least one polymer brush layer, attached to the at least one filtering membrane on a side downstream to a fluidic flow between the first chamber and the second chamber; and
magnetic nanoparticles in at least one chamber of the plurality of chambers,
wherein the magnetic nanoparticles comprise a polymer brush layer on their surfaces.
2. The device of claim 1, wherein the plurality of chambers comprises three chambers, a first filtering membrane between the first chamber and the second chamber, and a second filtering membrane between the second and a third chamber.
3. The device of claim 1, further comprising a first electrode in the first chamber and a second electrode in the second chamber, to provide fluidic flow by electrokinetic forces.
4. The device of claim 1, wherein the desired biological particle is a virus, a bacterium, cell, or cell waste.

5. The device of claim 1, further comprising two electrodes configured to apply an electrostatic potential to the plurality of chambers, thereby driving the fluidic flow by electrokinetic forces.

6. The device of claim 1, wherein the at least one polymer brush layer is made of polyethylene glycol.

7. The device of claim 1, further comprising a hydrogel polymer in at least one chamber of the plurality of chambers, the hydrogel polymer configured to apply osmotic pressure to the plurality of chambers.

8. The device of claim 7, wherein the hydrogel polymer is a hydrogel polymer scaffold.

9. A method comprising:
providing a plurality of chambers, at least one filtering membrane between a first chamber and a second chamber of the plurality of chambers, the at least one filtering membrane having a pore size based on a desired biological particle to be filtered, at least one polymer brush layer, attached to the at least one filtering membrane on a side downstream to a fluidic flow between the first chamber and the second chamber;
inserting a solution containing biological particles in the first chamber of the plurality of chambers;
driving the fluidic flow through the plurality of chambers; and
extracting the desired biological particle after filtering through the plurality of chambers,
wherein:
the plurality of chambers further comprises magnetic nanoparticles in at least one chamber of the plurality of chambers, and
the magnetic nanoparticles comprise a polymer brush layer on their surfaces.

10. The method of claim 9, wherein the plurality of chambers further comprises at least two electrodes, the method further comprising:
applying an electrostatic field to the plurality of chambers by the at least two electrodes, thereby driving the fluidic flow by electrokinetic forces.

11. The method of claim 9, wherein the plurality of chambers further comprises a hydrogel polymer in at least one chamber of the plurality of chambers, the method further comprising:
applying the osmotic pressure by the hydrogel polymer.

12. The method of claim 11, wherein the hydrogel polymer is a hydrogel polymer scaffold.

13. The method of claim 9, further comprising applying a magnetic field in at least one chamber of the plurality of chambers.

14. The method of claim 13, wherein applying a magnetic field comprises controlling a flow of the magnetic nanoparticles.

15. The method of claim 14, wherein controlling the flow of the magnetic nanoparticles comprises separating the magnetic nanoparticles from the biological particles.

* * * * *

UNITED STATES PATENT AND TRADEMARK OFFICE
CERTIFICATE OF CORRECTION

PATENT NO. : 9,861,939 B2
APPLICATION NO. : 14/874326
DATED : January 9, 2018
INVENTOR(S) : Sangil Kim et al.

Page 1 of 1

It is certified that error appears in the above-identified patent and that said Letters Patent is hereby corrected as shown below:

In the Specification

Under the title "STATEMENT OF INTEREST", Column 1, Lines 7-10, delete the paragraph "The United States Government has rights in this invention pursuant to Contract No. Contract No. DE-AC52-07NA27344 between the U.S. Department of Energy and Lawrence Livermore National Security, LLC." and replace with the paragraph "The United States Government has rights in this invention pursuant to Contract No. DE-AC52-07NA27344 between the United States Department of Energy and Lawrence Livermore National Security, LLC, for the operation of Lawrence Livermore National Laboratory."

Signed and Sealed this
Fifth Day of March, 2019

Andrei Iancu
*Director of the United States Patent and Trademark Office*